(12) United States Patent
Rimkus et al.

(10) Patent No.: US 8,586,091 B2
(45) Date of Patent: Nov. 19, 2013

(54) PHARMACEUTICAL COMPOSITION COMPRISING N-[3-CHLORO-4-[(3-FLUOROPHENYL)METHOXY]PHENYL]-6-[5[[[2-(METHYLSULFONYL)ETHYL]-AMINO]METHYL]-QUINAZOLINAMINE

(75) Inventors: Katrin Rimkus, München (DE); Frank Muskulus, Gröbenzell (DE); Sandra Brueck, Ottenhofen (DE); Jana Paetz, Moorenwies (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 13/060,750

(22) PCT Filed: Aug. 24, 2009

(86) PCT No.: PCT/EP2009/060890
§ 371 (c)(1),
(2), (4) Date: Aug. 31, 2011

(87) PCT Pub. No.: WO2010/023188
PCT Pub. Date: Mar. 4, 2010

(65) Prior Publication Data
US 2011/0305762 A1 Dec. 15, 2011

(30) Foreign Application Priority Data
Aug. 25, 2008 (EP) .................................. 08014984

(51) Int. Cl.
*A61K 9/14* (2006.01)
*A61K 31/517* (2006.01)
*A61P 35/04* (2006.01)

(52) U.S. Cl.
USPC ...................... 424/489; 544/293; 514/266.24

(58) Field of Classification Search
USPC ...................... 424/489; 544/293; 514/266.24
See application file for complete search history.

(56) References Cited

U.S. PATENT DOCUMENTS

| | | | | |
|---|---|---|---|---|
| 4,831,058 | A | * 5/1989 | Pankhania et al. | 514/570 |
| 2008/0026067 | A1 | 1/2008 | Kuwabe et al. | |
| 2011/0263852 | A1 * | 10/2011 | Jyothi Prasad et al. | 544/293 |
| 2012/0015965 | A1 * | 1/2012 | Rimkus et al. | 514/266.24 |

FOREIGN PATENT DOCUMENTS

| WO | WO 2004/087102 A2 * | 10/2004 | A61K 9/00 |
|---|---|---|---|
| WO | WO 2005/120504 A2 * | 12/2005 | A61K 31/4709 |
| WO | WO 2006/110811 | 10/2006 | |
| WO | WO 2006/113649 | 10/2006 | |
| WO | WO 2007/143483 | 12/2007 | |
| WO | WO 2008/067144 | 6/2008 | |

OTHER PUBLICATIONS

Glaxo Group, "Tyverb 250 mg", Gebrauchsinformation [Online], Jun. 2008.
Boyd, B. et al., "Lapatinib", *Drugs of the Future*, vol. 30, No. 12 (2005), pp. 1225-1239.
*Brockhaus Enzyklopädie*, FA Brockhaus, Mannheim, 19th edition, vol. 26, (1995), pp. 178-179.

(Continued)

*Primary Examiner* — Aradhana Sasan
(74) *Attorney, Agent, or Firm* — Chalin A. Smith; Smith Patent Consulting

(57) ABSTRACT

The present invention relates to a pharmaceutical composition comprising N-[3-chloro-4-[(3-fluorophenyl)methoxy] phenyl]-6-[5[[[2-(methylsulfonyl)ethyl]amino]methyl]-2-furyl]-4-quinazolinamine as active pharmaceutical ingredient and a process of preparing such composition.

10 Claims, 3 Drawing Sheets dissolution profile of the effervescent tablet formulation disclosed in example 1 (squares) compared to Tyverb® tablets (rhombi) (conditions: 900 ml 2 % Tween 80 in 0.1 N HCl pH 1, 0.1 mm flow cell, 37 °C, 75 rpm paddle)

(56) References Cited

OTHER PUBLICATIONS

Burris III, H., et al., "Dual Kinase Inhibition in the Treatment of Breast cancer: Initial Experience with the EGFR/ErbB-2 Inhibitor Lapatinib", *The Oncologist*, vol. 9, No. 3, (2004), pp. 10-15.

Burris III, H., et al., "Phase I Safety, Pharmacokinetics, and Clinical Activity Study of Lapatinib (GW572016), a Reversible Dual Inhibitor of Epidermal Growth Factor Receptor Tyrosine Kinases, in Heavily Pretreated Patients With Metastatic Carcinomas", *Journal of Clinical Oncology*, vol. 23, No. 23, (2005), pp. 5305-5313.

"Guidelines on the use of International Nonproprietary Names (INNs) for Pharmaceutical Substances", WHO, Geneva (1997), pp. 1-15.

"International Nonproprietary Names for Pharmaceutical Substances (INN)", WHO Drug Information, vol. 18, No. 1, (2004), pp. 83, 84 and 100.

Lachman, L. et al., *The Theory and Practice of Industrial Pharmacy*, Lea & Febiger, Philadelphia, 2nd edition, vol. 26, (1976), pp. 101 and 112.

Meeting highlights, "Highlights From: ECCO 13—The European Cancer Conference", *Clinical Breast Cancer*, (2005), pp. 380-384.

Parrott, E.L., *Pharmaceutical Technology: Fundamental Pharmaceutics*, Burgess Publishing Company, Minneapolis, 3rd edition, (1971), p. 344.

*Römpp Chemie Lexikon*, J. Falbe et al. editors, 10th edition, (1996-1999), pp. 268, 269, 1600, 3156, 4376, 4377.

*Rote Liste® 2009*, Herausgeber und Verlag, Frankfurt/Main, (2009*), pp. 86:195-86:196. (*editorial deadline for medicament applications was Sep. 2008).

Spector, N., et al., "Study of the Biologic Effects of Lapatinib, a Reversible Dual Inhibitor of ErbB1 and ErbB2 Tyrosine Kinase, on Tumor Growth and Survival Pathways in Patients With Advanced Malignancies", *Journal of Clinical Oncology*, vol. 23, No. 11, (2005), pp. 2502-2512.

TYKERB® product information, Mar. 2007.

* cited by examiner

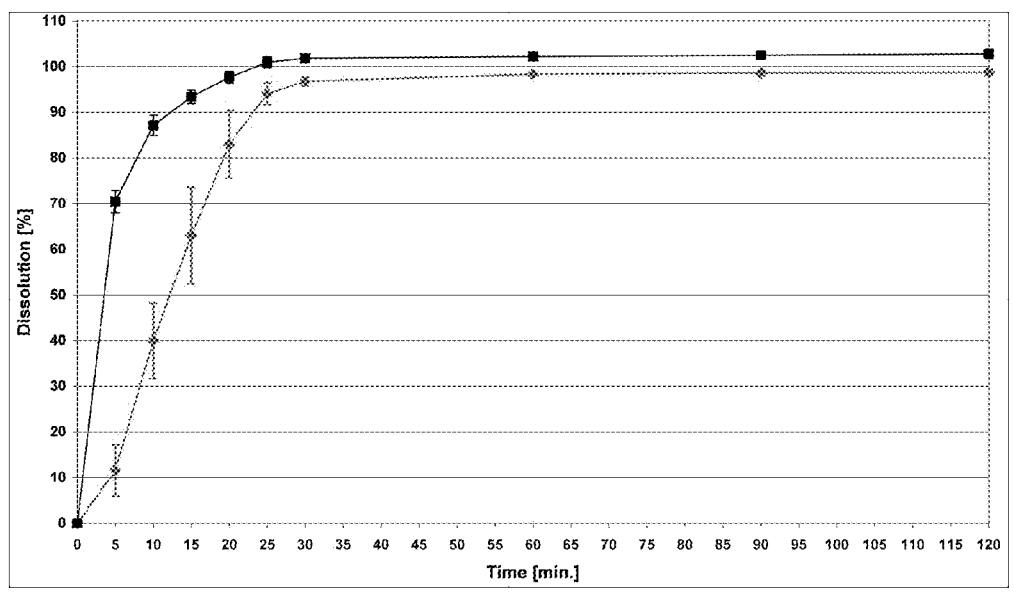
Figure 1: dissolution profile of the effervescent tablet formulation disclosed in example 1 (squares) compared to Tyverb® tablets (rhombi) (conditions: 900 ml 2 % Tween 80 in 0.1 N HCl pH 1, 0.1 mm flow cell, 37 °C, 75 rpm paddle)

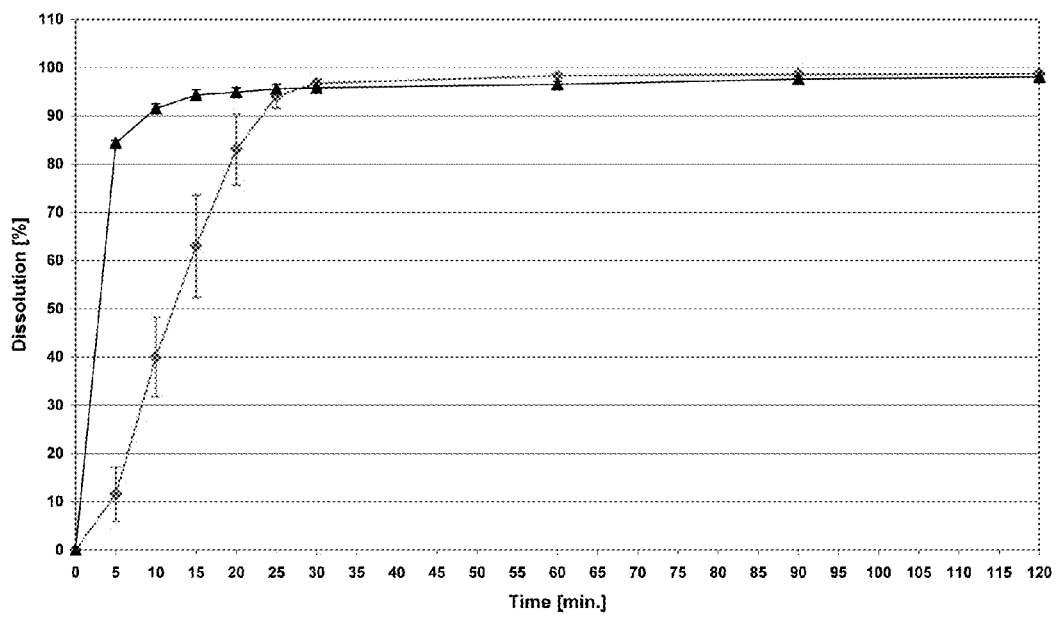
Figure 2: dissolution profile of the pellet formulation disclosed in example 3 (triangles) compared to Tyverb® tablets (rhombi) (conditions: 900 ml 2 % Tween 80 in 0.1 N HCl pH 1, 0.1 mm flow cell, 37 °C, 75 rpm paddle)

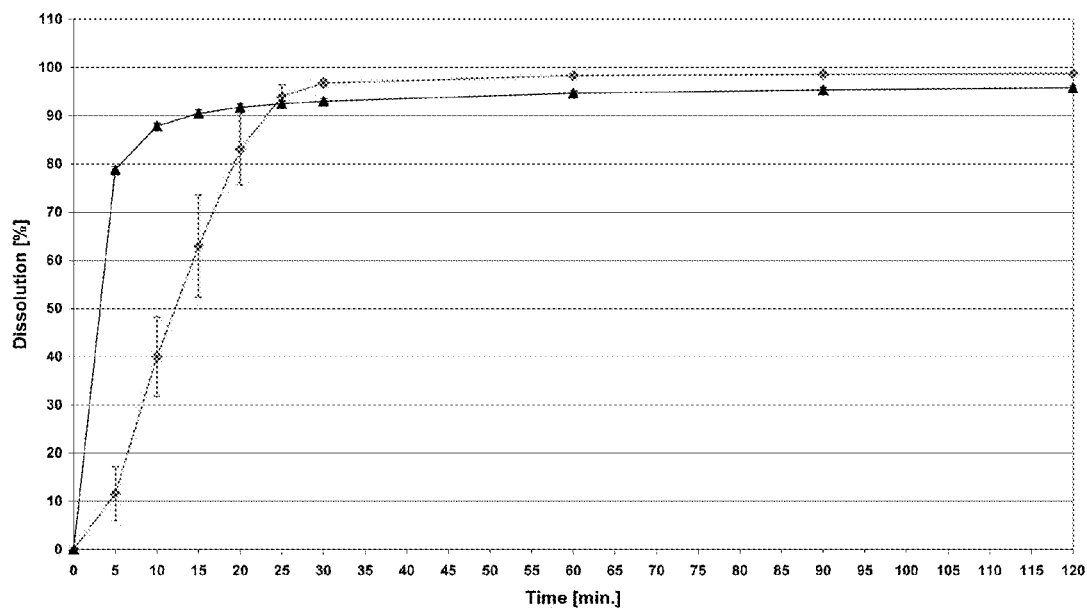
Figure 3: dissolution profile of the granulate formulation disclosed in example 4 (triangles) compared to Tyverb® tablets (rhombi) (conditions: 900 ml 2 % Tween 80 in 0.1 N HCl pH 1, 0.1 mm flow cell, 37 °C, 75 rpm paddle)

PHARMACEUTICAL COMPOSITION COMPRISING N-[3-CHLORO-4-[(3-FLUOROPHENYL)METHOXY]PHENYL]-6-[5[[[2-(METHYLSULFONYL)ETHYL]-AMINO]METHYL]-QUINAZOLINAMINE

This application corresponds to the national phase of International Application No. PCT/EP2009/060890 filed Aug. 24, 2009, which, in turn, claims priority to European Patent Application No. 08.014984.2 filed Aug. 25, 2008, the contents of which are incorporated by reference herein in their entirety.

FIELD OF THE INVENTION

The present invention relates to a pharmaceutical composition comprising N-[3-chloro-4-[(3-fluorophenyl)methoxy]phenyl]-6-[5[[[2-(methylsulfonyl)ethyl]amino]methyl]-2-furyl]-4-quinazolinamine as active pharmaceutical ingredient and a process of preparing such composition.

BACKGROUND OF THE INVENTION

The compound N-[3-chloro-4-[(3-fluorophenyl)methoxy]phenyl]-6-[5[[[2-(methylsulfonyl)ethyl]amino]methyl]-2-furanyl]-4-quinazolinamine (INN: Lapatinib) is a tyrosine kinase inhibitor which dually inhibits the growth factor receptors ErbB1 (epidermal growth factor receptor, EGFR) and ErbB2 (HER2). Lapatinib is a member of the 4-anilino-quinazoline class of kinase inhibitors that have been shown to bind to the ATP binding site of protein kinases and compete with the ATP substrate. This blocks receptor phosphorylation and activation, preventing subsequent downstream signalling events.

Lapatinib, in combination with Capecitabine, is indicated for the treatment of patients with advanced or metastatic breast cancer whose tumours overexpress ErbB2 (Her2) and who have received prior therapy including trastuzumab.

Lapatinib and its pharmaceutical effects on disorders like cancer are described in WO 1999/035146. Further medical uses of Lapatinib and its salts are inter alia known from WO 2005/120504, WO 2006/002422 and WO 2006/066267.

WO 1999/035146 discloses s process of preparing Lapatinib. According to this and other known manufacturing processes, Lapatinib is obtained as a solid. One of the forms of Lapatinib is its crystalline ditosylate salt as described in WO 2002/002552.

Conventional pharmaceutical Lapatinib formulations for oral administration are disclosed in WO 2006/113649.

Typically, Lapatinib is administered at a dose of 1250 mg once daily. Tablets comprising 250 mg Lapatinib (as ditosylate salt monohydrate) are sold under the brand name Tyverb® (by Glaxo Smith Kline). Thus, the required dosage is comprised in 5 Tyverb® tablets that have to be administered perorally once a day. This situation is unsatisfactory and inconvenient to the patient especially since cancer patients' medications usually consist of multiple drug regimen demanding the administration of large numbers of tablets or capsules where required along with an intravenous therapy. Further, these patients often suffer from nausea and lesions of the oral mucosa. Therefore the peroral application of drugs may be hampered by vomiting fits and swallowing problems. Hence, it would be desirable to facilitate the administration of the cancer patients' daily medication.

It is therefore an object of the invention to provide an improved alternative dosage form that is convenient to administer and that contains the whole daily Lapatinib medication in a unit dose.

Thus, the present invention relates to a pharmaceutical composition comprising N-[3-chloro-4-[(3-fluorophenyl)methoxy]phenyl]-6-[5[[[2-(methylsulfonyl)ethyl]amino]methyl]-2-furyl]-4-quinazolinamine or a pharmaceutically acceptable salt thereof wherein a unit dose of the composition contains 1200 to 1300 mg of the active pharmaceutical ingredient calculated as the free base.

DESCRIPTION OF THE INVENTION

N-[3-Chloro-4-[(3-fluorophenyl)methoxy]phenyl]-6-[5[[[2-(methylsulfonyl)ethyl]amino]-methyl]-2-furyl]-4-quinazolinamine (INN: Lapatinib) has the following chemical structure:

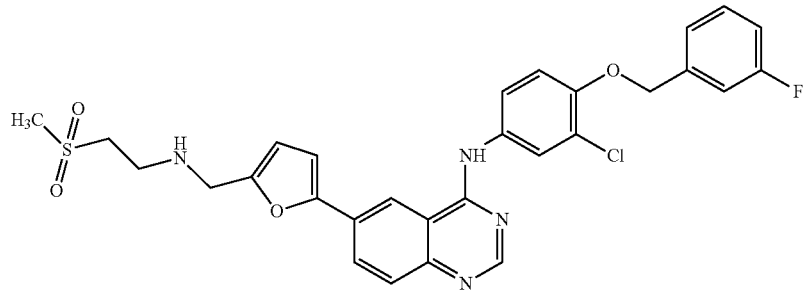 [SMILES: CS(=O)(=O)CCNCc1ccc(-c2ccc3ncnc(Nc4ccc(OCc5cccc(F)c5)c(Cl)c4)c3c2)o1]

Lapatinib can be readily synthesized using techniques well known in the art. Syntheses of Lapatinib are disclosed for example in WO 1999/035146.

Ditosylate salt forms of Lapatinib as well as processes for their manufacture are disclosed in WO 2002/002552.

The term "active pharmaceutical ingredient" (API) refers to Lapatinib and to pharmaceutically acceptable salt thereof. The API can be present in any polymorphic form, including solvates and hydrates. The Lapatinib ditosylate monohydrate form is especially preferred.

The active pharmaceutical ingredient may be present in the pharmaceutical composition in an amount of 10 to 70 wt. % based on the total weight of the composition.

Advantageous properties with respect to solubility, homogeneity, stability, flowability, compressibility and the avoidance of demixing tendencies are achieved if the active pharmaceutical ingredient used in the preparation of the pharmaceutical composition of the present invention has a mean particle size of 1 to 30 µm, preferably 1 to 20 µm, more preferably 1 to 15 µm. In one embodiment the active pharmaceutical ingredient has a specific surface area of 5 to 10 m²/g. The latter is measured according to the gas adsorption method (BET method), and the particle size distribution is determined via laser scattering performed on the API dispersed in a suspending medium. The above particle size range and/or the above specific surface area range are advantageous also with respect of a fast dissolution of a pharmaceutical composition containing a high drug load of more than 60 wt. %.

Since the active pharmaceutical ingredient as obtained from the manufacturing process may vary in its particle size, it might have to be milled or ground in order to obtain the desired mean particle size. The inventors have encountered problems with the grinding of Lapatinib ditosylate monohydrate due to its long needle shape. It was found that these problems can for example be overcome by adding one or more excipients to the milling or grinding procedure.

A bulk density of the pharmaceutical composition ranging from of 0.3 to 0.9 g/ml, preferably of 0.4 to 0.8 g/ml is advantageous.

The pharmaceutical composition of the invention preferably has a Hausner ratio in the range of 1.05 to 1.65, more preferably of 1.1 to 1.5. The Hausner ratio is the ratio of bulk density to tapped density.

The pharmaceutical composition of the present invention may further comprise one or more pharmaceutically acceptable excipients, such as fillers, binding agents, lubricants, flow enhancers, antisticking agents, disintegrating agents, effervescent agents, viscosity enhancing agent and solubilizers. As pharmaceutically acceptable excipients conventional excipients known to the person skilled in the art may be used. See for example "Lexikon der Hilfsstoffe für Pharmazie, Kosmetik and angrenzende Gebiete", edited by H. P. Fiedler, 4th Edition, Edito Cantor, Aulendorf and earlier editions, and "Handbook of Pharmaceutical Excipients", Third Edition, edited by Arthur H. Kibbe, American Pharmaceutical Association, Washington, USA, and Pharmaceutical Press, London.

Preferred examples of the fillers are lactose, mannitol, sorbitol or microcrystalline cellulose. The filler is suitably present in an amount of 0 to 80 wt. %, preferably of 10 to 50 wt. % of the total weight of the composition.

The binding agent can for example be microcrystalline cellulose (MCC) or hydroxypropylmethyl cellulose (HPMC). Preferably the binding agent is present in an amount of 1 to 25 wt. %, more preferably at 5 to 15 wt. % of the total weight of the composition.

The lubricant may for example be a stearate (e.g. zinc stearate, earth alkali metal stearate or sodium stearyl fumarate), talc, polytetrafluoroethylene, sodium benzoate, polyethylene glycol 8000, sodium oleate, succinic acid, adipic acid or fumaric acid. The lubricant is suitably present in an amount of 0.1 to 2 wt. %, preferably about 1 wt. % of the total weight of the composition.

Preferred disintegrating agents are croscarmellose sodium, sodium carboxymethyl starch or cross-linked polyvinylpyrrolidone (crospovidone). The disintegrating agent is suitably present in an amount of 0.1 to 20 wt. %, more preferably at about 0.5 to 7 wt. % of the total weight of the composition.

The flow enhancer can for example be colloidal silicon dioxide. Preferably, the flow enhancer is present in an amount of 0.5 to 8 wt. %, more preferably at 0.5 to 3 wt. % of the total weight of the composition.

The antisticking agent is for example talcum and may be present in amounts of 1 to 5%. wt, more preferably in an amount of 1.5 to 3 wt. % of the total weight of the composition.

The effervescent complex in effervescent formulations e.g. effervescent tablets most commonly consists of a soluble acid source and a carbonate source to produce carbon dioxide gas, the latter serving as disintegrant. The acidity needed for the effervescent reaction can be derived from food acids, acid anhydrides and acid salts. The food acid can for example be citric acid, tartaric acid, malic acid, fumaric acid, adipic acid or succinic acid. The acid anhydride may be succinic anhydride or citric anhydride. Acid salts are e.g. sodium dihydrogen phosphate (monosodium phosphate), disodium dihydrogen pyrophosphate (sodium acid pyrophosphate), acid citric salts (sodium dihydrogen citrate and disodium hydrogen citrate), sodium acid sulfite (sodium bisulfite). Suitable carbonate sources are for example sodium bicarbonate, sodium carbonate, potassium bicarbonate, potassium carbonate, sodium sesquicarbonate (mixture of equal molar amounts of sodium carbonate and sodium bicarbonate), glycine carbonate, L-lysine carbonate, arginine carbonate, calcium carbonate.

Alternatively, effervescence may be induced by the formation of other gases such as oxygen, e.g. released from sodium perborate or from a combination of e.g. a peroxygen compound that yields active oxygen on mixture with water (e.g. sodium perborate monohydrate or sodium percarbonate) and a chlorine compound that liberates hypochlorite on contact with water (e.g. sodium dichloroisocyanurate or calcium hypochlorite).

An effervescent complex consisting of citric acid and sodium bicarbonate is especially preferred.

Suitable viscosity enhancing agents are for example sugars such as sucrose, sugar alcohols such as sorbitol, polysaccharides (e.g. methyl cellulose, carboxymethyl cellulose, hydroxylethyl cellulose, agar agar, guar gum, tragacanth, alginates), proteins (e.g. gelatine), synthetic polymers such as polyvinyl derivatives, carboxyvinyl polymers, non polymeric gel forming substances (e.g. silicon dioxide) or glycerine.

An improvement of the solubility of the active pharmaceutical ingredient can for example be achieved by the addition complex forming agents/compounds (e.g. sodium benzoate, sodium salicylate or cyclodextrins), the alternation of solvent properties (e.g. by adding PVP or polyethylene glycols) or the addition of solubilizers which form tenside micelles (e.g. surfactants).

Suitable solubilizers are for example surfactants such as polyoxyethylene alcohol ethers (e.g. Brij®), polysorbates (e.g. Tween®) or polyoxypropylene polyoxyethylene copolymers (poloxamer; e.g. Pluronic®) and may be present in amounts of up to 7 wt. %, more preferably 0.02 to 2 wt. % of the total weight of the composition.

Alternatively, a pseudo-emulsifier can be used. Its mechanism of action mainly relies on an enhancement of viscosity. However, pseudo-emulsifiers also possess emulsifying properties. Preferred pseudo-emulsifiers of the present invention are for example cellulose ethers, gum Arabic or tragacanth and may be present in amounts of 1 to 10 wt. %, more preferably 3 to 7 wt. % of the total weight of the composition.

A person skilled in the art may use these or other excipients depending on the selected process of preparing the pharmaceutical composition of the invention.

The pharmaceutical composition of the present invention can be formulated in any known manner, provided it comprises a dosage amount of 1200-1300 mg, preferably about 1250 mg of Lapatinib free base per unit dose. Effervescent tablets, syrups, granulates and pellets are especially preferred.

The pharmaceutical composition of the present invention can be manufactured according to standard methods known in the art. Granulates and effervescent tablets according to the invention can be obtained by dry compaction or wet granulation. These granulates can subsequently be mixed with e.g. suitable disintegrating agents, glidants and lubricants and be compressed into tablets or filled into e.g. sachets of suitable size. Effervescent tablets can also be obtained by direct compression of a suitable powder mixture, i.e. without any preceding granulation of the excipients.

Suitable powder or granulate mixtures according to the invention are also obtainable by spray drying, lyophilization, melt extrusion, pellet layering, coating of the active pharmaceutical ingredient or any other suitable method. Preferably, the conditions are chosen such as to prevent amorphization of the active pharmaceutical ingredient. The so obtained powders or granulates can be mixed with one or more suitable ingredients and the resulting mixtures can either be compressed to form effervescent tablets or filled into sachets.

Pellets according to the invention are obtainable by standard methods including granulation and extrusion techniques. The so obtained pellets can be mixed with one or more suitable ingredients and the resulting mixtures can be filled into sachets.

Syrups according to the present invention can be obtained according to standard methods known in the art. The syrups are preferably based on alcohol free liquids, most preferably water.

FIGURES

FIG. 1 shows dissolution profile of the effervescent tablet obtained in example 1.

FIG. 2 shows dissolution profile of the pellet formulation obtained in example 3.

FIG. 3 shows dissolution profile of the granulate obtained in example 4.

EXAMPLES

The invention is illustrated in the following examples which are not to be constructed as being limiting. The amounts of ingredients are given as amounts per single unit dose.

Example 1

Effervescent Tablet

| ingredient | amount [mg] |
|---|---|
| Lapatinib ditosylate monohydrate | 2037.16 |
| sucrose | 815 |
| sodium bicarbonate | 500 |
| citric acid, anhydrous | 250 |
| sodium sulfate decahydrate | 400 |
| sodium stearyl fumarate (Pruv ®) | 38 |
| PVP (Kollidon ® VA64) | 5 |
| sodium saccharin | 3 |
| Pluronic ® F68 | 2 |

Lapatinib ditosylate monohydrate, citric acid, sucrose and Pluronic were mixed and sieved. This mixture was wet granulated with a solution of saccharin in purified water. A second granulate was prepared by mixing and sieving sodium saccharin, sodium bicarbonate and sodium sulfate and wet granulating these with a solution of PVP in ethanol and water. The two dried granulates were mixed and compressed into tablets.

These tablets were intended for the preparation of a suspension, e.g. in water.

The dissolution of the effervescent tablets was fast and complete (see FIG. 1) and superior as compared to the reference (Tyverb® tablets). After 5, 10, 15 and 20 minutes 70.4%, 87.1%, 93.4% and 97.7% of the active pharmaceutical ingredient were dissolved from the effervescent tablet, compared to only 11.6%, 40%, 63% and 83% from the reference product.

Example 2 a

Syrup

| ingredient | amount [mg] |
|---|---|
| Lapatinib ditosylate monohydrate | 2037.16 |
| sorbitol (Neosorb ®) | 1600 |
| purified water | 4000 |
| orange aroma | 100 |
| PVP (Kollidon ® CL-SF) | 38 |
| sodium saccharin | 20 |
| Cremophor ® RH40 | 40 |

Cremophor was dissolved in purified water, and sodium saccharin, sorbitol and PVP were successively added. Lapatinib ditosylate monohydrate was suspended in this mixture, which was then filled into glass bottles of suitable size. The daily Lapatinib dosage of 1250 mg was contained in 10.4 g of the so obtained syrup.

Example 2 b

Syrup

| ingredient | amount [mg] |
|---|---|
| Lapatinib ditosylate monohydrate | 2037.16 |
| sorbitol (Neosorb ®) | 1600 |
| purified water | 9780 |
| orange aroma | 100 |
| PVP (Kollidon ® CL-SF) | 38 |
| sodium saccharin | 20 |
| Pluronic ® F68 | 40 |

Pluronic® F68 was dissolved in 40.9% of the purified water, and sodium saccharin, sorbitol, PVP and the residual water were successively added. Lapatinib ditosylate monohydrate was suspended in this mixture, which was then filled into glass bottles of suitable size. The daily Lapatinib dosage of 1250 mg was contained in 14.08 g of the so obtained syrup.

Example 3

Pellets

| ingredient | amount [mg] |
|---|---|
| Lapatinib ditosylate monohydrate | 2037.16 |
| lactose (Tablettose ® 80) | 965 |
| Pluronic ® F68 | 10 |

Lapatinib ditosylate monohydrate and lactose were mixed and sieved and then wetted with a solution of Pluronic® F68 in purified water. The wet mixture was extruded and the resulting pellets were dried and filled into sachets of suitable size.

These pellets were intended for the preparation of a suspension by adding a suitable liquid, e.g. water.

The dissolution of the pellets was faster than that of the reference (Tyverb®) tablets). After 5, 10, 15 and 20 minutes 84.4%, 91.6%, 94.3 and 94.9% of the active pharmaceutical ingredient were dissolved from the formulation, compared to only 11.6%, 40%, 63% and 83% from the reference product.

Example 4

Granulate

| ingredient | amount [mg] |
| --- | --- |
| Lapatinib ditosylate monohydrate | 2037.16 |
| sorbitol (Neosorb ®) | 1913 |
| crospovidone (Kollidon ® CL-M) | 300 |
| Pluronic ® F68 | 20 |
| sodium saccharin | 20 |
| orange aroma | 10 |

Lapatinib ditosylate monohydrate, Sorbitol and Crospovidone were mixed, sieved and wet granulated with a solution of Pluronic® F68, sodium saccharin and orange aroma in purified water. The granulate was dried and filled into sachets of suitable size.

This granulate was intended for the preparation of a suspension by adding a suitable liquid, e.g. water.

The dissolution of the granulate was faster than that of the reference (Tyverb®) tablets). After 5, 10, 15 and 20 minutes 78.8%, 87.9, 90.5% and 91.8% of the active pharmaceutical ingredient were dissolved from the formulation, compared to only 11.6%, 40%, 63% and 83% from the reference product.

The invention claimed is:

1. A unit dose of a pharmaceutical composition comprising an active pharmaceutical ingredient selected from the group consisting of N-[3-chloro-4-[(3-fluorophenyl)methoxy]-phenyl]-6-[5[[[2-(methylsulfonyl)ethyl]amino]methyl]-2-furyl]-4-quinazolinamine and pharmaceutically acceptable salts thereof, wherein said unit dose contains 1200 to 1300 mg of said active pharmaceutical ingredient calculated as the free base, further wherein said active pharmaceutical ingredient has a specific surface area of 5 to 10 $m^2/g$.

2. The unit dose according to claim 1, wherein the active pharmaceutical ingredient is the ditosylate salt of N-[3-chloro-4-[(3-fluorophenyl)methoxy]phenyl]-6-[5[[[2-(methylsulfonyl)ethyl]amino]methyl]-2-furyl]-4-quinazolinamine.

3. The unit dose according to claim 1, wherein said active pharmaceutical ingredient has a particle size of 1 to 30 μm.

4. The unit dose according to claim 1, wherein said pharmaceutical composition is in form of an effervescent tablet.

5. The unit dose according to claim 1, wherein said pharmaceutical composition is in form of a syrup.

6. The unit dose according to claim 1, wherein said pharmaceutical composition is in form of granulates suitable for suspension.

7. The unit dose according to claim 1, wherein said pharmaceutical composition is in form of pellets suitable for suspension.

8. A process for preparing the unit dose according to claim 1, wherein said process comprises the step of milling or grinding the active pharmaceutical ingredient in the presence of one or more excipients.

9. The unit dose according to claim 1, wherein the active pharmaceutical ingredient is the ditosylate salt of N-[3-chloro-4-[(3-fluorophenyl)methoxy]phenyl]-6-[5[[[2-(methylsulfonyl)ethyl]amino]methyl]-2-furyl]-4-quinazolinamine in its monohydrate form.

10. The unit dose according to claim 1, wherein said active pharmaceutical ingredient has a particle size of 1 to 20 μm.

* * * * *

UNITED STATES PATENT AND TRADEMARK OFFICE
CERTIFICATE OF CORRECTION

PATENT NO. : 8,586,091 B2
APPLICATION NO. : 13/060750
DATED : November 19, 2013
INVENTOR(S) : Katrin Rimkus et al.

Page 1 of 1

It is certified that error appears in the above-identified patent and that said Letters Patent is hereby corrected as shown below:

Title page, item (54) and in the Specifications, Column 1, correct the title to read: "PHARMACEUTICAL COMPOSITION COMPRISING N [3-CHLORO-4-[(3-FLUOROPHENYL)METHOXY]PHENYL]-6-[5[[[2-(METHYLSULFONYL) ETHYL]AMINO]METHYL]-2-FURYL]-4-QUINAZOLINAMINE".

Signed and Sealed this
Eighteenth Day of March, 2014

Michelle K. Lee
*Deputy Director of the United States Patent and Trademark Office*